United States Patent [19]
Walker

[11] Patent Number: 4,671,285
[45] Date of Patent: Jun. 9, 1987

[54] TREATMENT OF HUMAN NEUROLOGICAL PROBLEMS BY LASER PHOTO SIMULATION

[76] Inventor: Judith Walker, 1964 Westwood Blvd., Los Angeles, Calif. 90025

[21] Appl. No.: 886,769

[22] Filed: Jul. 16, 1986

Related U.S. Application Data

[63] Continuation of Ser. No. 824,535, Jan. 31, 1986, abandoned, which is a continuation of Ser. No. 602,326, Apr. 20, 1984, abandoned.

[51] Int. Cl.⁴ .............................................. A61N 5/00
[52] U.S. Cl. .................................................. 128/395
[58] Field of Search ...................... 128/303.1, 395–398

[56] References Cited

U.S. PATENT DOCUMENTS 3,900,034  8/1975  Katz et al. ........................... 128/395

FOREIGN PATENT DOCUMENTS 2371935  6/1978  France ............................... 128/395

*Primary Examiner*—Lee S. Cohen
*Attorney, Agent, or Firm*—Spensley Horn Jubas & Lubitz

[57] ABSTRACT

This invention relates to a method of treating nerve damages in humans, and more particularly, to a noninvasive, nontraumatic method which comprises the steps of applying an essentially monochromatic light to the skin area adjacent to the damaged nerve region of the body.

9 Claims, 2 Drawing Figures

TREATMENT OF HUMAN NEUROLOGICAL PROBLEMS BY LASER PHOTO SIMULATION

This is a continuation of application Ser. No. 824,535 filed on Jan. 31,1986, now abandoned, which is a continuation of application Ser. No. 602,326 filed on Apr. 20, 1984, now abanodned.

BACKGROUND OF THE INVENTION

1. Field of the Invention

The present invention relates to a method of treating nerve damage in humans.

2. Prior Art

There are a great many injuries which take place each year causing damage to various components of the nervous system. For example, there are approximately 500,000 spinal cord injuries in the United States, with an estimated 15,000 new injuries per year. Many of these injuries produce severe pain and limit movement. It is generally agreed by neurologists that the largest obstacle to movement is spasticity. The rigidity of spasticity produces massive resistance to movement, and flexor spasms as well as clonus can become a stimulus to awaken the victim in the middle of the night and can become very painful. Unfortunately, the treatment of spasticity has not been very good. The existing method consists of the administration of various drugs which may have significant adverse side effects. Neurosurgical intervention such as epidural spinal cord stimulation has met with limited success, but generally this approach is considered only as a last resort. In addition, neurosurgery in at least some instances has resulted in even more severe pain than that originally experienced by the patient. While physical therapy does offer certain advantages in that it is noninvasive, it is also time consuming, expensive and has only limited effectiveness. Yet another method is referred to as transcutaneous nerve stimulation (TNS) which has been used in the treatment of chronic and trackable pain but its use is generally limited and its effectiveness is not well documented.

Thus, prior art methods tend to be limited both in their effectiveness, and in terms of their expense, ease of application and the like. Thus, there has long existed a need for an noninvasive, nontraumatic method of treating nerve damage, especially in the central nervous system, such as due to trauma, infection, inflammation and the like.

BRIEF SUMMARY OF THE INVENTION

The present invention relates to the use of essentially monochromatic light to aid in the recovery from peripheral and central nervous system injury. The purpose of this invention is to provide neurological improvement in patients who have had damage done to their central or peripheral nervous system. In terms of the type of injury to which this methodology is applicable, the same would include trauma, infection, inflammation, congenital problems such as cerebral palsy, and vascular accident patients.

Patients who have the above disorders present a variety of neurological signs depending upon the location of the injury, including spasticity, clonus, paralysis, loss of sensation, a specific kind of pain (deafferentation pain), bowel and bladder incontinence, difficulty speaking or swallowing and intention tremor. Exposure of the skin overlying the peripheral nerves by a monochromatic light as described herein has resulted in improvements in all of the above signs except for bladder and bowel incontinence.

The present invention is also directed to the use of monochromatic light in the treatment of damage to the peripheral nerves including damage to the nerve root due to the demyelinating disease, neuralgia, neuropathy, radiculopathy, and damage due to acute infection such as shingles.

It should be appreciated that pain is a complex disorder and the use of the methodology described herein is directed to that pain which is the result of nerve injury. In particular, central nervous system injury such as damage to the spinal cord results in deafferentation pain, which is believed to be the result of epileptic-like activity produced by aberrant spinal cord neurons. This aberrant activity is perceived as pain by the central nervous system. This kind of pain has several characteristics which distinguish it from other common kinds of pain. More specifically, 1. The pain is intractable, and generally unresponsive to drugs, particularly narcotic medication, transcutaneous nerve stimulation, and other modalities for treating chronic pain.

2. The pain is generally described as burning, constant, and is often associated with an increase in spasticity, and 3. The pain always occurs below the level of the lesion.

By the use of the method of the present invention, a significant decrease in pain can be achieved.

The novel features which are believed to be characteristic of this invention, both as to its organization and method of operation, together with further objectives and advantages thereof, will be better understood from the following description considered in connection with the accompanying drawings in which a presently preferred embodiment of the invention is illustrated by way of examples. It is to be expressly understood, however, that the drawings are for the purpose of illustration and description only and are not intended as the definition of the limits of the invention.

DETAILED DESCRIPTION OF THE INVENTION

Figure 1:
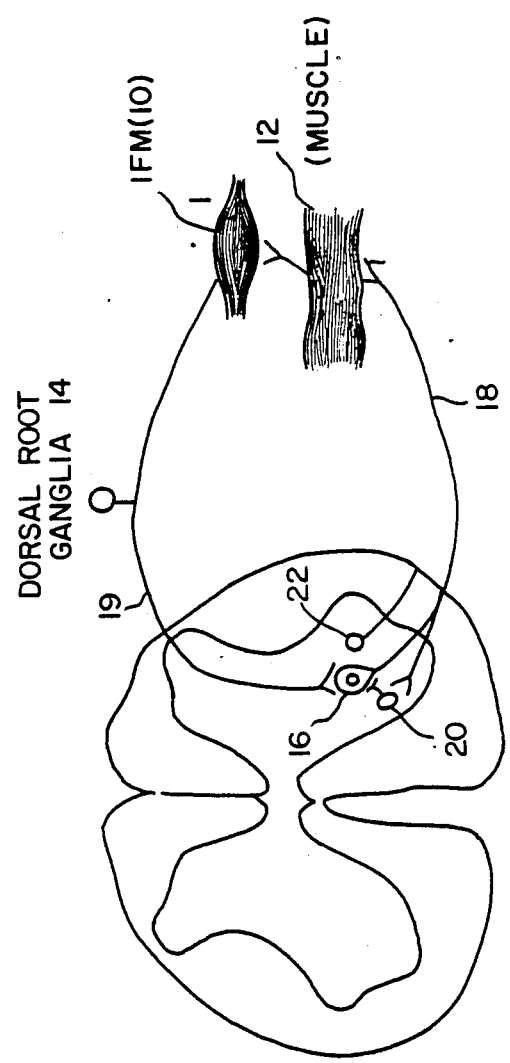
FIG. 1 is a partial diagram of the basic stretch reflex.

It is well established that there are biomedical applications of laser light which rely on the fact that exposure to monochromatic light results in heating, and even in vaporization. The immediate effect of low powered lasers, however, are nonthermal and result in a number of metabolic consequences. Some studies suggest that laser irradiation stimulates nerves via a nonthermal mechanism. For example, very brief exposure to an argon laser alters the firing pattern of isolated abdominal ganglion cells in Aplysia, and short pulses of irradiation with a ruby laser enhance release of acetylcholine from isolated Auerbach's plexus. These alterations are believed to be due to a non-thermal mechanism. The changes occur before a measurable increase in temperature in these preparations, and heating does not produce similar biological changes.

In recent double-blind trials, brief irradiation with a high-powered neodymium laser decreased pain and increased the range of motion in patients with rheumatoid arthritis. However, the use of high-power laser is thought to be hazardous.

The use of a low-power laser in the treatment of damage to the peripheral and central nervous system is of great importance, because such lasers are considered not to be significant risk devices. It is believed that the longer wavelengths across the visible-infrared spectrum penetrates the dermis to a greater extent than short wavelengths. Red light is thought to penetrate to approximately a 500 micrometer depth in the human hand, which absorbs light maximally in the 500–600 nanometer range would thus absorb a helium-neon laser irradiation (632.5 nanometers). Furthermore, the radiation of human skin with such a laser results in a reproducible electrophysiological response from the underlying nerve as measured by the somatosensory evoked potential. In the present invention monochromatic light is used having a wavelength of 632.5 nm. It should be understood that other wavelengths are also within the scope of this invention. Further, while monochromatic light is preferably used, it should be understood that multiple wavelengths of light can also be used, wherein each wavelength is targeted for a specific chromophore.

As indicated above, the instant invention relates to treating nervous system injuries. Some of these injuries exhibit a phenomenon known as clonus. Clonus is a 5–7 hertz pathological oscillation exhibited by spastic muscles after being passively stretched. After initiation of a tendon jerk, the muscle relaxes and stretches the spindles which resume an afferent discharge. This discharge causes the alpha-motor neurons to discharge again, producing more reflex contractions of muscle. In neurologically intact spinal cords, input from muscle spindles is insufficient to initiate such cyclical discharge. In spastic muscle, however, hyper-excitability of the spinal cord is such that synchronus spindle firing produces cyclic alpha-motor neuron discharge which results in reflex contraction. Such a closed oscillating feedback loop indicates the importance of inhibitory control mechanisms that normally promote assynchrony of neural activity.

Referring now to FIG. 1, a diagram illustrating the stretching of intrafusal muscle is set forth.

Stretching of intrafusal muscle (IFM) 10, 12 produces firing of the stretch receptor 10 which has its cell body in the dorsal root ganglion 14 whose axon 19 terminates on the alpha motoneuron 16. Activation of the stretch receptor 10 results in firing of alpha motoneurons 16, which in turn produces muscle contraction and deceases activity of the stretch receptor 10 of the IFM. The axon 18 of the alpha motoneuron sends a collateral to a Renshaw cell 20 which inhibits the homonymous alpha motoneuron. The sensitivity of the stretch receptor 10 is also regulated by gamma efferents 22, which are under bulbospinal control. Multiple inhibitory and excitatory factors regulate the output of the alpha motoneuron preventing the cylic discharge that produces clonus.

As set forth below, clonus has significantly been reduced when certain areas of the body, especially the affected area and/or those peripheral nerves which have a great impact on the central nervous system function are treated with monochromatic light.

METHODOLOGY AND TEST RESULTS

Twenty one subjects with chronic traumatic spinal cord injury were selected. After complete physical examination and routine laboratory tests (electrolytes, BUN, creatinine, etc.), the tests were conducted. Every third patient was assigned to one of two control groups. Patients with decubitus ulcers, chronic pain, or urinary tract infections were excluded from the study because these factors may become potent stimuli for producing clonus. Subjects with associated peripheral nerve injuries were also excluded. The subjects were determined to be drug-free for three months before enrolling in the study, except for the use of antibiotics. All these patients had ankle clonus that persisted for 40–300 beats or contractions after passive stretch.

The identification of peripheral nerve sites was performed as follows:

The radial nerve was located 4 centimeters proximal to the wrist flexure under the belly of the extensor indicis muscle. The usual location of the median nerve between the palmaris longus tendons was not used because preliminary evidence in three patients indicated that the presence of these tendons prevented the transmission of light to the underlying nerve. For this reason, an alternate location for the median nerve proximal to the styloid process was used. The ulnar nerve was located in the ulnar groove 4 centimeters proximal to the wrist flexure. The saphenous nerve was located at the metatarsal cuneiform junction and at the heel.

Experimental Group

Seven subjects received irradiation with a helium-neon laser (632.5 nanometers, 1 milliwatt, 20 hertz) by a fiber optic probe held against the subject's skin. A 0.4 square meter of skin overlying the radial, median, ulnar and saphenous nerves was irradiated bilaterally for 40 seconds to each site. Neither the subject, nor the nurse performing the procedure, knew which therapy was experimental and which represented sham stimulation. These tests were carried out for five days.

Control Group I

Seven subjects were exposed to sham laser from an instrument which looks identical to the helium-neon laser apparatus, which in fact emitted no light. This apparatus was designed specifically for this purpose. The fiber optic probe was placed on each peripheral nerve site for 40 seconds. The subjects also closed their eyes during the sham laser administration.

Control Group II

Seven subjects received laser radiation for 40 seconds to skin not innervated by these peripheral nerves. These patients were also asked to close their eyes during this procedure, and received irradiation on the same schedule as the subjects receiving experimental and sham treatment.

In addition to the subject receiving laser or control treatments, five subjects received electrical stimulation of these peripheral nerves for 45 minutes and five received stimulation for one hour as previously described. Ten control subjects received stimulation to areas of skin on the forearm and ankle not directly supplied by these nerves for 45 minutes or one hour.

Measurement Of Clonus

Clonus was elicited by brisk dorsiflexion of the foot by a physical therapist who did not know to which group this subject had been assigned. A clonus count was performed before treatment and at various intervals after irradiation. In order to facilitate comparison between the subjects, the number of beats recorded after irradiation was expressed as a percent of the number of beats recorded before laser treatment. Thus, a score of 100% (number of beats after treatment/number of beats before treatment times 100%) indicates no change in the number of beats whereas a score of 0% indicates complete clonus suppression.

One hour of electrical stimulation produced complete suppression of clonus as measured 30 minutes after cessation of stimulation. On the other hand, 45 minutes of stimulation produces only partial suppression, indicating that there is a relationship between the duration of stimulation and magnitude of the effect. This is illustrated in FIG. 2.

Figure 2:
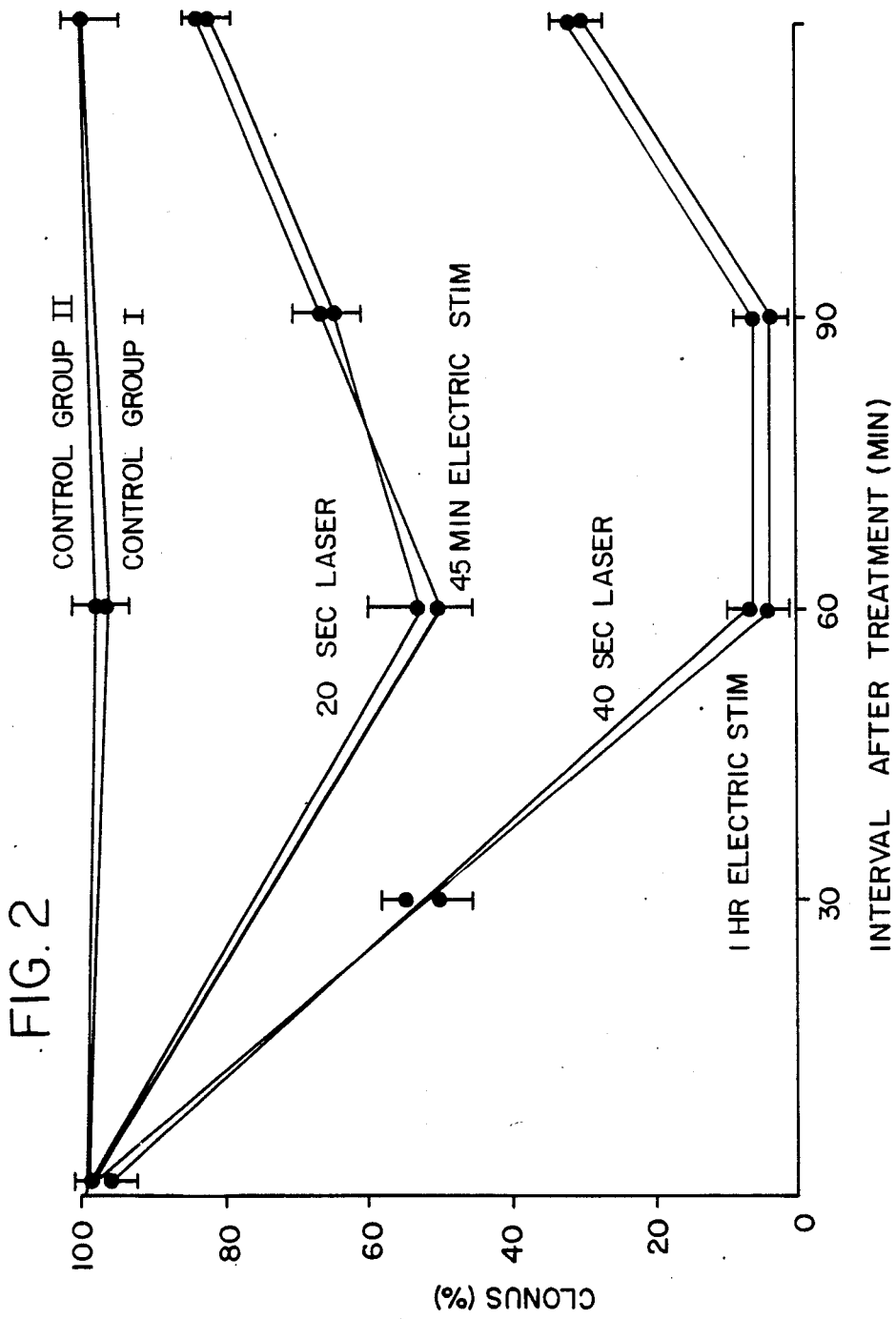
FIG. 2 is a graph showing time course of clonus surpression or electrical stimulation.

FIG. 2: Time course for inhibition of clonus by electrical stimulation or laser irradiation. Subjects were given 45 minutes or one hour of eletrical stimulation to peripheral nerve sites or received 20 or 40 sec. of laser exposure to the skin overlying the peripheral nerves. Control group 1 received sham irradiation while control group 11 received 40 sec. of irradiation to skin not overlying these peripheral nerves. Clonus was expressed as percentage of beats before treatment.

Laser irradiation also appeared to suppress clonus beginning 30 minutes after cessation of irradiation. With an irradiation time of 20 seconds to skin overlying each peripheral nerve site, partial suppression occurs. However, increasing the exposure time to 40 seconds produces total suppression of clonus in a fashion identical to that observed after one hour of electrical stimulation. Sham irradiation (Control Group 1) or irradiation of skin not overlying these peripheral nerves (Control Group 2) had no effect. Thus, 40 seconds of irradiation to the skin overlying each nerve produced effects on clonus suppression of the same magnitude as seen after one hour of electrical stimulation.

40 seconds of irradiation to the right radial, median, ulnar and saphenous nerves produced clonus inhibition in the left side for as long as 90 minutes after cessation of treatment. However, inhibition occurred bilaterally 2 hours after cessation of treatment. Stimulation on the left side produced the opposite pattern of response. Sham irradiation (Control Group 1) or irradiation of skin not overlying peripheral nerve sites (Control Group 2) administered unilaterally had no effect on clonus measured subsequently on either side. Thus, irradiation appears to produce its effects on spinal cord excitability by the activation of precise neuroanatomical pathways.

Additional Tests and Results

Yet additional tests have been performed in which low power monochromatic light was used to treat nerve damage. For example, patients with cerebellar damage were treated with a low-power laser as outlined above. Greatly improved hand function and dexerity was observed after the first treatment. Patients with peripheral nerve damage to various locations of the body were treated with low-power monochromatic light by local application for 30 seconds to the affected area. Improved sensations were reported accompanied by normalization of electromyographic difficiencies. Patients with acute shingles accompanied by blisters had monochromatic light applied to the affected area for three minutes on three separate occasions. Improvements in the blisters as well as a marked reduction of pain was reported. Eighty patients with trigeminal neuralgia were treated with monochromatic light from a helium-neon laser as discussed above. These patients were treated for 10 weeks and received 3 treatments per week. A double blind study was performed under normal medical supervision. After the first 3 weeks, those who received light treatment did significantly better in terms of decreased pain, use of medication, and had increased functional activities as compared to those who received placebo. After 10 weeks, the differences between the groups were even more dramatic. Patients with paralysis due to traumatic spinal cord injury were treated with monochromatic light 7 to 10 times per day for 1 to 6 months. Improvements in hand function, trunk stability and leg function were noted and documented with the use somatosensory evoked potentials.

To understand the effects of laser irradiation the optical properties of the skin will now be discussed. Skin has chromophores (optically active molecules). Each of these molecules exhibits its own characteristic absorption spectrum. All chromophores, whether found in the skin or elsewhere, have several common characteristics. They are highly resonant ringed structures with a molecular weight of less than 500. The greater the number of rings, the longer the wavelengths absorbed. There are a large number of possible chromophores available in myelin, neuronal membranes and intraneuronally. Interaction of helium-neon laser irradiation or other similar monochromatic light source with a pre-sent population of chromophores is believed to result in changes in the ionic permeability and this leads to depolarization.

The existence of a population of wavelength-specific neurochromophores leads to several conclusions: (1) the effects of light on neuralactivity are relatively wavelength specific, and (2) at a given wavelength, prolonged exposure to very low powered laser light would exert biological effects identical to that observed after a very brief irradiation with a high powered laser. Exposure to 488 nm argon laser, 694 ruby laser as well as helium-neon laser have all been shown to alter neuronal activity. Irradiation with infrared laser (1090 nm) had no effect. Thus, wavelengths in the 488–694 nm range are believed to be most active in stimulating neurons. It should also be understood that the essentially monochromatic light as discussed herein includes light with a ±50 nm wavelength range, having a power of less than 100 miliwatts, and preferably about 1–3 miliwatts.

The present results indicate that the peripheral nervous system possesses a previously unsuspected degree of photo-sensitivity. The notion that the generation of an action potential by the wavelength specific interaction of a set of neuronal chromophores with light represents an experimentally verifiable model.

As one can see, the benefits of this invention have been demonstrated to have a pronounced effect in the treatment of neurological damage. It should be understood that while the preferred embodiment of the invention is set forth above, it will be apparent to one skilled in the art that other changes and modifications can be made without departing from the spirit and scope of the present invention as described and claimed herein.

I claim:

1. A method of treating disease of or damage to the central nervous system in humans involving pain or limitations of body movements comprising the steps of applying an essentialy monochromatic light having a non-traumatic power density to the skin area adjacent to a specific peripheral nerve region of the body and for sufficent time so as to achieve a decrease in pain or a reduction in muscle spasms.

2. A method according to claim 1 wherein said light is essentially red light.

3. A method according to claim 2 wherein said light has a wavelength approximately 632.5 nm.

4. The method according to cliam 1 wherein the light is red coherent light.

5. A method according to claim 1 wherein said light is applied to a 0.4 mm$^2$ area of skin for approximately 10 to 40 seconds at repeated intervals.

6. A method according to claim 1 wherein said light is applied to the skin area adjacent the radial, median, ulnar and saphenous nerves.

7. A method of treating clonus resultant from damage to or disease of the saphenous spinal cord in human patients comprising:
  irradiation with monochromatic light the skin overlying at least one of the radial, median, ulnar, or saphenous nerves at sufficient irradtion powr density and for sufficient time so as to achieve at least 50% reduction in said clonus.

8. The method of treating cerebellar damage resulting in impaired hand function and dexterity in human patients comprising:
  irradiating with monochromatic light the skin overlying at least one peripheral nerve of said patient at sufficient irradiation power density and for sufficient time so as to achieve improved hand function and dexterity.

9. The method of treating accute shingles in patients comprising:
  irradiating with monochromatic light the skin overlying at least one peripheral nerve of said patient at sufficient irradiation power density and for sufficient time so as to achieve improvements in blisters and reduction of pain.

* * * * *